(12) United States Patent
Chappa et al.

(10) Patent No.: US 9,283,350 B2
(45) Date of Patent: Mar. 15, 2016

(54) COATING APPARATUS AND METHODS

(71) Applicant: SurModics, Inc., Eden Prairie, MN (US)

(72) Inventors: Ralph A. Chappa, Ham Lake, MN (US); Timothy M. Kloke, Victoria, MN (US)

(73) Assignee: SurModics, Inc., Eden Prairie, MN (US)

( * ) Notice: Subject to any disclaimer, the term of this patent is extended or adjusted under 35 U.S.C. 154(b) by 0 days.

(21) Appl. No.: 14/063,124

(22) Filed: Oct. 25, 2013

(65) Prior Publication Data

US 2014/0161964 A1    Jun. 12, 2014

Related U.S. Application Data

(60) Provisional application No. 61/734,788, filed on Dec. 7, 2012.

(51) Int. Cl.
| | | |
|---|---|---|
| *B05C 1/06* | (2006.01) | |
| *B05C 13/02* | (2006.01) | |
| *A61M 25/00* | (2006.01) | |

(Continued)

(52) U.S. Cl.
CPC ....... *A61M 25/0009* (2013.01); *A61M 25/1029* (2013.01); *B05C 1/00* (2013.01); *B05C 1/06* (2013.01); *B05C 13/02* (2013.01); *A61M 2025/1031* (2013.01); *Y10S 901/43* (2013.01)

(58) Field of Classification Search
None
See application file for complete search history.

(56) References Cited

U.S. PATENT DOCUMENTS

| | | |
|---|---|---|
| 1,281,672 A | 10/1918 | Schorn |
| 1,866,100 A | 7/1932 | Hach |

(Continued)

FOREIGN PATENT DOCUMENTS

| | | |
|---|---|---|
| CA | 2351016 | 12/2001 |
| DE | 3335502 | 9/1983 |

(Continued)

OTHER PUBLICATIONS

U.S. Appl. No. 10/976,193,, "Notice of Allowance mailed Mar. 8, 2011", 6 Pgs.

(Continued)

*Primary Examiner* — Dah-Wei D Yuan
*Assistant Examiner* — Jethro M Pence
(74) *Attorney, Agent, or Firm* — Pauly, Devries Smith & Deffner, L.L.C.

(57) ABSTRACT

Embodiments of the invention include coating apparatuses and related methods. In an embodiment, the invention includes a coating apparatus. The coating apparatus can include a motor, a rotating contact member, a fluid applicator, a fluid pump, and a base member. The fluid applicator can include an orifice. The rotating contact member can be configured to rotate around a device to be coated that does not rotate. The rotating contact member can be configured to move along the lengthwise axis of a device to be coated. In an embodiment, the invention includes a method of coating a medical device. The method of coating a medical device can include a rotating a contact member around the outer diameter of a non-rotating medical device, applying a coating solution to the outer diameter of the non-rotating medical device at a position adjacent to the contact member, and moving at least one of the contact member and the non-rotating medical device with respect to one another so that the contact member moves with respect to the lengthwise axis of the non-rotating medical device. Other embodiments are also included herein.

21 Claims, 6 Drawing Sheets

(51) Int. Cl.
*A61M 25/10* (2013.01)
*B05C 1/00* (2006.01)

(56) References Cited

U.S. PATENT DOCUMENTS

| | | | |
|---|---|---|---|
| 2,330,880 A | 10/1943 | Gladfelter et al. | |
| 2,493,787 A | 1/1950 | Torretti | |
| 2,781,280 A * | 2/1957 | Miller | 427/482 |
| 3,198,170 A | 8/1965 | Toshio | |
| 3,318,281 A | 5/1967 | Plegat | |
| 3,935,896 A | 2/1976 | Tegtmeier et al. | |
| 3,963,069 A | 6/1976 | Marti et al. | |
| 4,051,805 A | 10/1977 | Waldrum | |
| 4,060,116 A | 11/1977 | Frailly | |
| 4,073,335 A | 2/1978 | Fort et al. | |
| 4,075,975 A | 2/1978 | Oswald | |
| 4,153,201 A | 5/1979 | Berger et al. | |
| 4,174,678 A | 11/1979 | Van Den Bergh | |
| 4,195,637 A | 4/1980 | Gruntzig et al. | |
| 4,240,373 A | 12/1980 | Anger | |
| 4,289,089 A | 9/1981 | Tacke et al. | |
| 4,301,968 A | 11/1981 | Berger et al. | |
| 4,337,896 A | 7/1982 | Berger et al. | |
| 4,352,459 A | 10/1982 | Berger et al. | |
| 4,375,820 A | 3/1983 | Vinarcsik et al. | |
| 4,503,802 A | 3/1985 | Keller et al. | |
| 4,541,564 A | 9/1985 | Berger et al. | |
| 4,567,934 A | 2/1986 | Nakao et al. | |
| 4,572,451 A | 2/1986 | Ikeda et al. | |
| 4,638,045 A | 1/1987 | Kohn et al. | |
| 4,655,393 A | 4/1987 | Berger | |
| 4,723,708 A | 2/1988 | Berger et al. | |
| 4,743,252 A | 5/1988 | Martin, Jr. et al. | |
| 4,978,067 A | 12/1990 | Berger et al. | |
| 5,041,089 A | 8/1991 | Mueller et al. | |
| 5,087,246 A | 2/1992 | Smith | |
| 5,102,402 A | 4/1992 | Dror et al. | |
| 5,183,509 A | 2/1993 | Brown et al. | |
| 5,219,120 A | 6/1993 | Ehrenberg et al. | |
| 5,304,121 A | 4/1994 | Sahatjian | |
| 5,318,587 A | 6/1994 | Davey | |
| 5,382,234 A | 1/1995 | Cornelius et al. | |
| 5,387,247 A | 2/1995 | Vallana et al. | |
| 5,413,638 A | 5/1995 | Bernstein, Jr. et al. | |
| 5,501,735 A | 3/1996 | Pender | |
| 5,527,389 A | 6/1996 | Rosenblum et al. | |
| 5,571,089 A | 11/1996 | Crocker | |
| 5,643,362 A | 7/1997 | Garves | |
| 5,656,332 A | 8/1997 | Saito et al. | |
| 5,658,387 A | 8/1997 | Reardon et al. | |
| 5,743,964 A | 4/1998 | Pankake | |
| 5,776,101 A | 7/1998 | Goy | |
| 5,807,331 A | 9/1998 | Den Heijer et al. | |
| 5,833,891 A | 11/1998 | Subramaniam et al. | |
| 5,837,008 A | 11/1998 | Berg et al. | |
| 5,837,088 A | 11/1998 | Palmgren et al. | |
| 5,882,336 A | 3/1999 | Janacek | |
| 5,882,405 A | 3/1999 | Kish et al. | |
| 5,897,911 A | 4/1999 | Loeffler | |
| 6,019,784 A | 2/2000 | Hines | |
| 6,153,252 A | 11/2000 | Hossainy et al. | |
| 6,156,373 A | 12/2000 | Zhong et al. | |
| 6,203,551 B1 | 3/2001 | Wu | |
| 6,203,732 B1 | 3/2001 | Clubb et al. | |
| 6,245,099 B1 | 6/2001 | Edwin et al. | |
| 6,254,921 B1 | 7/2001 | Chappa et al. | |
| 6,322,847 B1 | 11/2001 | Zhong et al. | |
| 6,333,595 B1 | 12/2001 | Horikawa et al. | |
| 6,345,630 B2 | 2/2002 | Fishkin et al. | |
| 6,358,556 B1 | 3/2002 | Ding et al. | |
| 6,368,658 B1 | 4/2002 | Schwarz et al. | |
| 6,394,995 B1 | 5/2002 | Solar et al. | |
| 6,395,326 B1 | 5/2002 | Castro et al. | |
| 6,406,754 B2 | 6/2002 | Chappa et al. | |
| 6,431,770 B1 | 8/2002 | Kurematsu et al. | |
| 6,435,959 B1 | 8/2002 | Skrmetta | |
| 6,506,437 B1 | 1/2003 | Harish et al. | |
| 6,517,515 B1 | 2/2003 | Eidenschink | |
| 6,517,889 B1 | 2/2003 | Jayaraman | |
| 6,521,299 B1 | 2/2003 | Dessauer | |
| 6,527,863 B1 | 3/2003 | Pacetti et al. | |
| 6,544,582 B1 | 4/2003 | Yoe | |
| 6,555,157 B1 | 4/2003 | Hossainy | |
| 6,562,136 B1 | 5/2003 | Chappa et al. | |
| 6,565,659 B1 | 5/2003 | Pacetti et al. | |
| 6,572,644 B1 | 6/2003 | Moein | |
| 6,605,154 B1 | 8/2003 | Villareal | |
| 6,607,598 B2 | 8/2003 | Schwarz et al. | |
| 6,616,765 B1 | 9/2003 | Castro et al. | |
| 6,623,504 B2 | 9/2003 | Vrba et al. | |
| 6,656,529 B1 | 12/2003 | Pankake | |
| 6,669,980 B2 | 12/2003 | Hansen | |
| 6,673,154 B1 | 1/2004 | Pacetti et al. | |
| 6,676,987 B2 | 1/2004 | Zhong et al. | |
| 6,695,920 B1 | 2/2004 | Pacetti et al. | |
| 6,709,514 B1 | 3/2004 | Hossainy | |
| 6,709,712 B2 | 3/2004 | Chappa et al. | |
| 6,723,373 B1 | 4/2004 | Narayanan et al. | |
| 6,725,901 B1 | 4/2004 | Kramer et al. | |
| 6,743,462 B1 | 6/2004 | Pacetti | |
| 6,743,463 B2 | 6/2004 | Weber et al. | |
| 6,783,793 B1 | 8/2004 | Hossainy et al. | |
| 6,803,070 B2 | 10/2004 | Weber | |
| 6,818,063 B1 | 11/2004 | Kerrigan | |
| 6,896,842 B1 | 5/2005 | Hamilton et al. | |
| 6,981,982 B2 | 1/2006 | Armstrong et al. | |
| 7,010,933 B2 | 3/2006 | Ishitomi et al. | |
| 7,045,015 B2 | 5/2006 | Renn et al. | |
| 7,125,577 B2 | 10/2006 | Chappa | |
| 7,163,523 B2 | 1/2007 | Devens, Jr. et al. | |
| 7,192,484 B2 | 3/2007 | Chappa et al. | |
| 7,198,675 B2 | 4/2007 | Fox et al. | |
| 7,335,314 B2 | 2/2008 | Wu | |
| 7,563,324 B1 | 7/2009 | Chen et al. | |
| 7,611,532 B2 | 11/2009 | Bates et al. | |
| 7,669,548 B2 | 3/2010 | Chappa | |
| 7,958,840 B2 | 6/2011 | Chappa | |
| 8,632,837 B2 | 1/2014 | Gong et al. | |
| 2,253,019 A1 | 8/2014 | Crepeau | |
| 2001/0001824 A1 | 5/2001 | Wu | |
| 2002/0051730 A1 | 5/2002 | Bodnar et al. | |
| 2002/0082679 A1 | 6/2002 | Sirhan et al. | |
| 2002/0094440 A1 | 7/2002 | Llanos et al. | |
| 2002/0103526 A1 | 8/2002 | Steinke | |
| 2002/0115400 A1 | 8/2002 | Skrmetta | |
| 2002/0155212 A1 | 10/2002 | Hossainy | |
| 2003/0003221 A1 | 1/2003 | Zhong et al. | |
| 2003/0044514 A1 | 3/2003 | Richard | |
| 2003/0054090 A1 | 3/2003 | Hansen | |
| 2003/0059520 A1 | 3/2003 | Chen et al. | |
| 2003/0059920 A1 | 3/2003 | Drohan et al. | |
| 2003/0088307 A1 | 5/2003 | Shulze et al. | |
| 2003/0113439 A1 | 6/2003 | Pacetti et al. | |
| 2003/0150380 A1 | 8/2003 | Yoe | |
| 2003/0157241 A1 | 8/2003 | Hossainy et al. | |
| 2003/0190420 A1 | 10/2003 | Chappa et al. | |
| 2004/0062875 A1 | 4/2004 | Chappa et al. | |
| 2004/0073298 A1 | 4/2004 | Hossainy | |
| 2004/0081745 A1 | 4/2004 | Hansen | |
| 2004/0161547 A1 | 8/2004 | Carlson et al. | |
| 2004/0185168 A1 | 9/2004 | Weber et al. | |
| 2004/0194704 A1 | 10/2004 | Chappa et al. | |
| 2004/0213893 A1 | 10/2004 | Boulais | |
| 2005/0098097 A1 | 5/2005 | Chen et al. | |
| 2005/0142070 A1 | 6/2005 | Hartley | |
| 2005/0158449 A1 | 7/2005 | Chappa | |
| 2006/0020295 A1 | 1/2006 | Brockway et al. | |
| 2006/0029720 A1 | 2/2006 | Panos et al. | |
| 2006/0045981 A1 * | 3/2006 | Tsushi et al. | 427/428.01 |
| 2006/0064134 A1 | 3/2006 | Mazar et al. | |
| 2006/0064142 A1 | 3/2006 | Chavan et al. | |
| 2006/0074404 A1 | 4/2006 | Struble | |
| 2006/0088653 A1 | 4/2006 | Chappa | |
| 2006/0096535 A1 | 5/2006 | Haller et al. | |

(56) References Cited

U.S. PATENT DOCUMENTS

| | | |
|---|---|---|
| 2006/0111754 A1 | 5/2006 | Rezai et al. |
| 2006/0116590 A1 | 6/2006 | Fayram et al. |
| 2006/0165872 A1 | 7/2006 | Chappa et al. |
| 2006/0191476 A1* | 8/2006 | Nagase et al. ............... 118/258 |
| 2007/0101933 A1 | 5/2007 | Chappa |
| 2007/0116855 A1 | 5/2007 | Fox et al. |
| 2007/0131165 A1 | 6/2007 | Fox et al. |
| 2007/0141232 A1 | 6/2007 | Tochterman et al. |
| 2007/0259100 A1 | 11/2007 | Guerriero et al. |
| 2007/0259102 A1 | 11/2007 | Mcniven et al. |
| 2008/0149025 A1 | 6/2008 | Swenson |
| 2008/0274266 A1 | 11/2008 | Davis et al. |
| 2009/0018643 A1 | 1/2009 | Hashi et al. |
| 2009/0090299 A1 | 4/2009 | Menendez et al. |
| 2009/0269481 A1 | 10/2009 | Chappa et al. |
| 2010/0040766 A1 | 2/2010 | Chappa et al. |
| 2010/0055294 A1 | 3/2010 | Wang et al. |
| 2010/0070020 A1 | 3/2010 | Hashi et al. |
| 2010/0227044 A1 | 9/2010 | Scheer |
| 2011/0281019 A1 | 11/2011 | Gong et al. |
| 2011/0281020 A1 | 11/2011 | Gong et al. |
| 2011/0311713 A1 | 12/2011 | O'neill et al. |
| 2012/0315376 A1 | 12/2012 | Nguyen et al. |
| 2013/0337147 A1 | 12/2013 | Chappa et al. |
| 2014/0121597 A1 | 5/2014 | Chappa et al. |
| 2014/0328998 A1 | 11/2014 | Chappa et al. |

FOREIGN PATENT DOCUMENTS

| | | |
|---|---|---|
| EP | 144873 | 6/1985 |
| WO | 00/01322 | 1/2000 |
| WO | 01/32382 | 5/2001 |
| WO | 02/20174 | 3/2002 |
| WO | 03/004072 | 1/2003 |
| WO | 2004028579 | 4/2004 |
| WO | 2004028699 | 4/2004 |
| WO | 2004037126 | 5/2004 |
| WO | 2004037443 | 5/2004 |
| WO | 2007100801 | 9/2007 |
| WO | 2008002357 | 1/2008 |
| WO | 2009132214 | 10/2009 |
| WO | 2010024898 | 3/2010 |
| WO | 2010146096 | 12/2010 |
| WO | 2013181498 | 12/2013 |
| WO | 2014066760 | 5/2014 |
| WO | 2014182833 | 11/2014 |

OTHER PUBLICATIONS

Examiner's Answer, from U.S. Appl. No. 12/109,139, mailed Mar. 22, 2013, 12 pages.

"Final Office Action", mailed Dec. 28, 2011 in co pending U.S. Appl. No. 12/109,139, "Coating Application System With Shaped Mandrel," (6 Pages)., 6.

"Final Office Action", mailed Sep. 4, 2012 in U.S. Appl. No. 12/109,139, "Coating Application System With Shaped Mandrel," (8 pages)., 8.

"International Preliminary Report on Patentability", for PCT Application No. PCT/US2013/043547, mailed on Dec. 11, 2014 (7 pages).

"International Search Report and Written Opinion", for PCT/US2013/066810, mailed Apr. 17, 2014 (18 pages).

"International Search Report and Written Opinion", for PCY/US2013/043547, mailed Oct. 1, 2013 (10 pages).

"Invitation to Pay Additional Fees and, Where Applicable, Protest Fee", for PCT/US2013/066810, mailed Feb. 7, 2014 (6 pages).

"Invitation to Pay Additional Fees", for PCT Application No. PCT/US2014/037179, mailed on Oct. 24, 2014 (5 pages).

"Non Final Office Action mailed Jul. 14, 2011 in co pending U.S. Appl. No. 12/109,139, "Coating Application System With Shaped Mandrel" (9 pages)", 9 Pgs.

"Non-Final Office Action", mailed Apr. 4, 2012in co-pending U.S. Appl. No. 12/109,139, "Coating Application System With Shaped Mandrel," (8 pages)., 8.

"Office Action Mailed Jul. 9, 2007 for U.S. Appl. No. 11/539,443".

Office Action Mailed on Oct. 6, 2005 for U.S. Appl. No. 10/976,348.

"Office Action Mailed on Feb. 22, 2006 for U.S. Appl. No. 10/976,348".

"Office Action Mailed on May 17, 2007 for U.S. Appl. No. 10/976,193".

"Office Action Mailed on Jun. 13, 2006 for U.S. Appl. No. 10/976,193".

"Pct International Search Report and Written Opinion from International Application No. PCT/US2005/038628, corresponding to U.S. Appl. No. 10/976,193, mailed Mar. 22, 2006, pp. 1-16".

PCT International Search Report and Written Opinion from International Application No. PCT/US2009/041575, corresponding to U.S. Appl. No. 12/109,139, mailed Jul. 22, 2009, pp. 1-15.

"Pct Notification Concerning Transmittal of International Preliminary Report on Patentability from International Application No. PCT/US2005/038628, corresponding to U.S. Appl. No. 10/976,193, mailed May 10, 2007, pp. 1-10".

"Pto-892 Mailed Jul. 9, 2007 for U.S. Appl. No. 11/539,443".

"Pto-892 Mailed on Oct. 6, 2005 for U.S. Appl. No. 10/976,348".

"Pto-892 Mailed on May 17, 2007 for U.S. Appl. No. 10/976,193".

"Restriction Requirement", for U.S. Appl. No. 13/906,599, mailed on Dec. 3, 2014 (6 pages).

"Restriction Requirement", mailed Apr. 29, 2011 in co pending U.S. Appl. No. 12/109,139, "Coating Application System With Shaped Mandrel," (7 pages)., 7 Pgs.

* cited by examiner

COATING APPARATUS AND METHODS

This application claims the benefit of U.S. Provisional Application No. 61/734,788 filed Dec. 7, 2012, the content of which is herein incorporated by reference in its entirety.

FIELD OF THE INVENTION

The present invention relates to coating apparatuses and related methods. More specifically, the present invention relates to coating apparatus for coating medical devices including a rotating contact member.

BACKGROUND OF THE INVENTION

Functional improvements to implantable or insertable medical devices can be achieved by coating the surface of the device. For example, a coating formed on the surface of the device can provide improved lubricity, improved biocompatibility, or drug delivery properties to the surface. In turn, this can improve movement of the device in the body, extend the functional life of the device, or treat a medical condition near the site of implantation. However, various challenges exist for the design and use of coating apparatus designed to provide coatings to medical devices.

Traditional coating methods, such as dip coating, are often undesirable as they may result in flawed coatings that could compromise the function of the device or present problems during use. These methods can also result in coating inaccuracies, which can be manifested in variable amounts of the coated material being deposited on the surface of the device. When a drug is included in the coating material, it is often necessary to deliver precise amounts of the agent to the surface of the device to ensure that a subject receiving the coated device receives a proper dose of the agent. It has been difficult to achieve a great degree of accuracy using traditional coating methods and machines.

SUMMARY OF THE INVENTION

Embodiments of the invention include coating apparatus and related methods. In an embodiment, the coating apparatus can include a motor, a rotating contact member, a fluid applicator, a fluid pump, and a base member. The fluid applicator can include an orifice. The orifice of the fluid applicator can be disposed adjacent to the rotating contact member. The rotating contact member can be in mechanical communication with the motor. The rotating contact member can be configured to rotate around a device to be coated that does not rotate. The rotating contact member can be configured to move along the lengthwise axis of a device to be coated. The fluid pump can be in fluid communication with the fluid applicator. The base member can support the rotating contact member and the fluid applicator.

In an embodiment, the invention includes a method of coating a medical device. The method of coating a medical device can include rotating a contact member around the outer diameter of a non-rotating medical device. The method can further include applying a coating solution to the outer diameter of the non-rotating medical device at a position adjacent to the contact member. The method can further include moving at least one of the contact member and the non-rotating medical device with respect to one another so that the contact member moves with respect to the lengthwise axis of the non-rotating medical device.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE FIGURES

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Based on structural characteristics, certain types of medical device are more difficult to coat than others. By way of example, some devices cannot be easily spin-coated even though they include a long shaft based on their characteristics and shape. For example, devices that have some curvature and cannot be straightened out generally cannot be coated with apparatus that require spinning of the device. As such, these devices have been traditionally coated using techniques such as dip coating. However, dip coating suffers from at least three drawbacks. First, dip coating is a relatively slow process making it expensive. Second, because dip coating requires a large container or vat of material to dip into, there is frequently a large amount of coating material that is wasted in the form of a residual volume in the container into which the device is dipped. Third, dip coating can result in various coating irregularities including thickness variation, webbing, and the like.

Apparatus disclosed herein can be used to coat device that would otherwise be coated using dip-coating or device spin-coating techniques. In specific, coating apparatus herein can include a rotating contact member that rotates around the outer diameter of a device to be coated and applying a coating material while the device to be coated remains substantially rotationally stationary. The apparatus can be moved along the lengthwise axis of the device to be coated (and/or the device to be coated can be moved relative to the apparatus) while the rotating contact member rotates around the device to be coated applying the coating. The apparatus can coat the device regardless of shapes such as curvature since only a relatively small length of the device to be coated is in the apparatus at any given time and thus the device does not need to be substantially straight over its entire length as would normally be required if the device were being coated with an apparatus where the device itself was spun.

Figure 1:
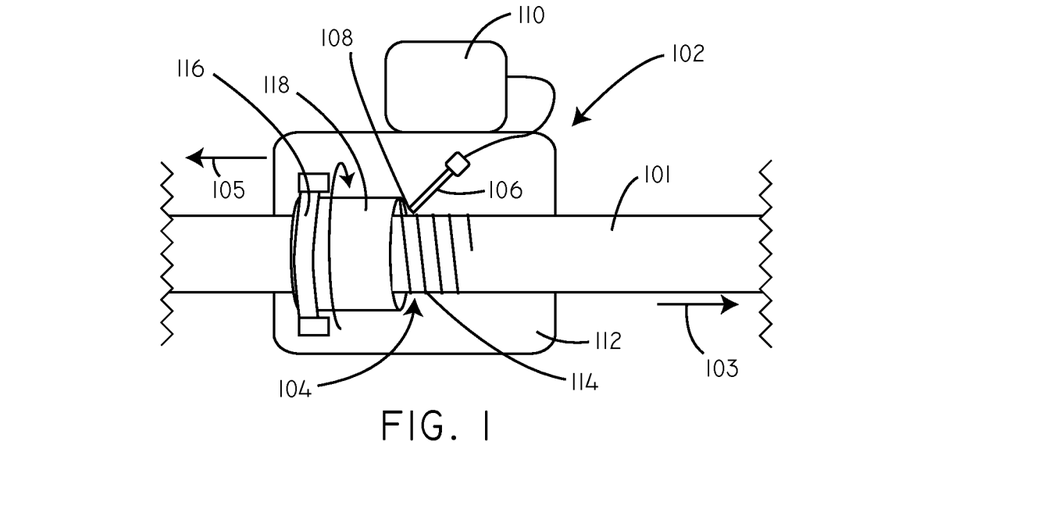
FIG. 1 is a schematic view of a coating apparatus in accordance with various embodiments herein.

FIG. 1 is a schematic view of a coating apparatus 102 in accordance with various embodiments herein. The coating apparatus 102 includes a rotating contact member 104, a fluid applicator 106, a fluid pump 110, and a base member 112. The fluid applicator 106 includes an orifice 108. In operation, the fluid pump 110 can cause a coating solution to pass through the fluid applicator 106 and out of the orifice 108 and onto a medical device 101 to be coated. While FIG. 1 shows the orifice positioned to deposit coating material near the trailing edge of the drive shaft, it will be appreciated that the orifice can also be positioned in other locations to deposit the coating material. Also, while in some embodiments the orifice is on the top side of the medical device, it will be appreciated that it can also be located on the side or the bottom. The rotating contact member 104 can include a spiral-shaped element 114. The coating apparatus 102 can include a mounting structure 116. The mounting structure 116 can allow the rotating contact member 104 to rotate. The mounting structure 116 can include bearings, bushings, or the like. The coating apparatus 102 can further include a drive shaft 118. In some embodiments, the drive shaft 118 can be a part of the rotating contact member 104. The medical device 101 can move in the direction of arrow 103 with respect to the coating apparatus 102. Alternatively, the coating apparatus 102 can move in the direction of arrow 105 with respect to the medical device 101. In some embodiments, both the coating apparatus 102 and the medical device 101 can move with respect to each other.

Figure 2A:
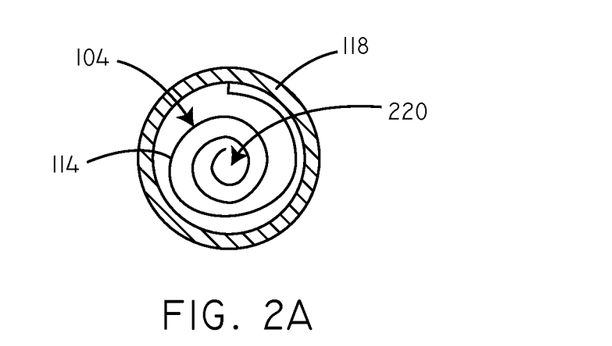
FIG. 2A is a front view of a drive shaft and rotating contact member of a coating apparatus in accordance with various embodiments herein.

FIG. 2A is a front view of a drive shaft and rotating contact member of a coating apparatus in accordance with various embodiments herein. The rotating contact member 104 can include spiral-shaped element 114. The rotating contact member 104 can define a channel 220. The channel 220 can be sized to accommodate a medical device 101 (not shown) as described in FIG. 1. The coating apparatus 102 can include drive shaft 118.

Figure 2B:
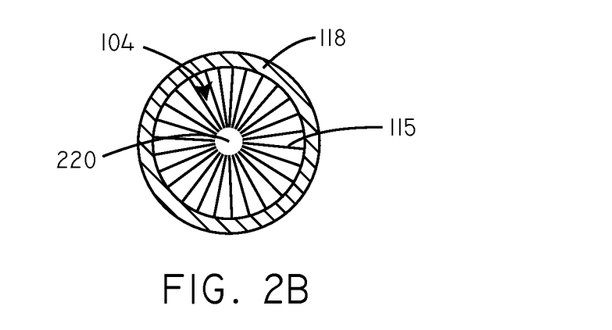
FIG. 2B is a front view of a drive shaft and rotating contact member of a coating apparatus in accordance with various embodiments herein.

In some embodiments, the rotating contact member can include a plurality of bristles and/or a brush. FIG. 2B is a front view of a drive shaft and rotating contact member of a coating apparatus in accordance with various embodiments herein. The rotating contact member 104 can include bristles 115. The bristles 115 can be oriented circumferentially around the rotating contact member 104 with an inward bias in some embodiments. In some embodiments the bristles 115 can be connected to drive shaft 118 or a similar structure that rotates. The rotating contact member 104 can define a channel 220. The channel 220 can be sized to accommodate a medical device 101 (not shown) as described in FIG. 1.

Figure 3A:
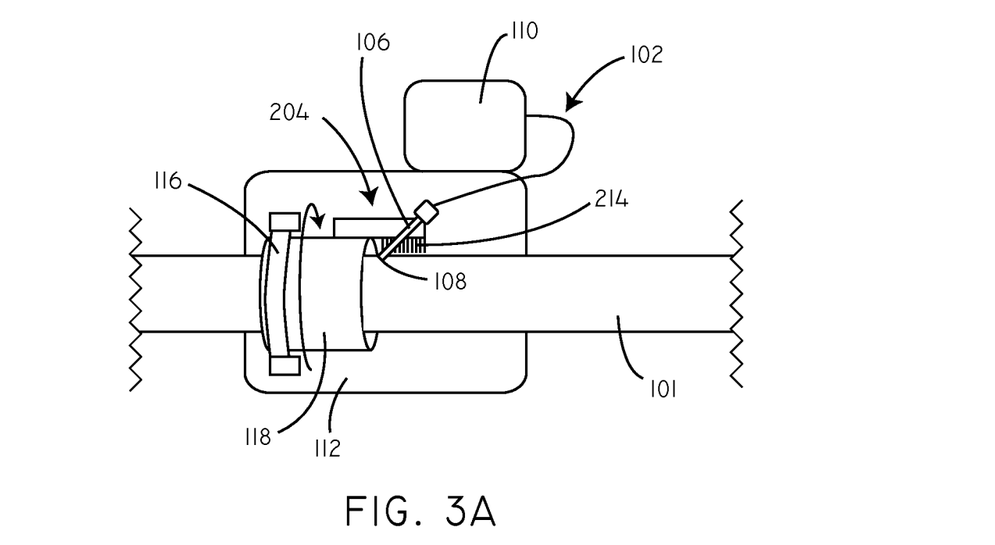
FIG. 3A is a schematic view of a coating apparatus in accordance with various embodiments herein.

FIG. 3A is a schematic view of a coating apparatus in accordance with various embodiments herein. The coating apparatus 102 includes a rotating contact member 204, a fluid applicator 106, a fluid pump 110, and a base member 112. The fluid applicator 106 includes an orifice 108. The coating apparatus 102 can include mounting structure 116. The coating apparatus 102 can include drive shaft 118. The rotating contact member 204 can include a brush 214 or similar brush-like structure. The brush 214 can contact the surface of the medical device 101 to be coated as the rotating contact member 204 rotates around and contacts the medical device 101 to be coated.

Figure 3B:
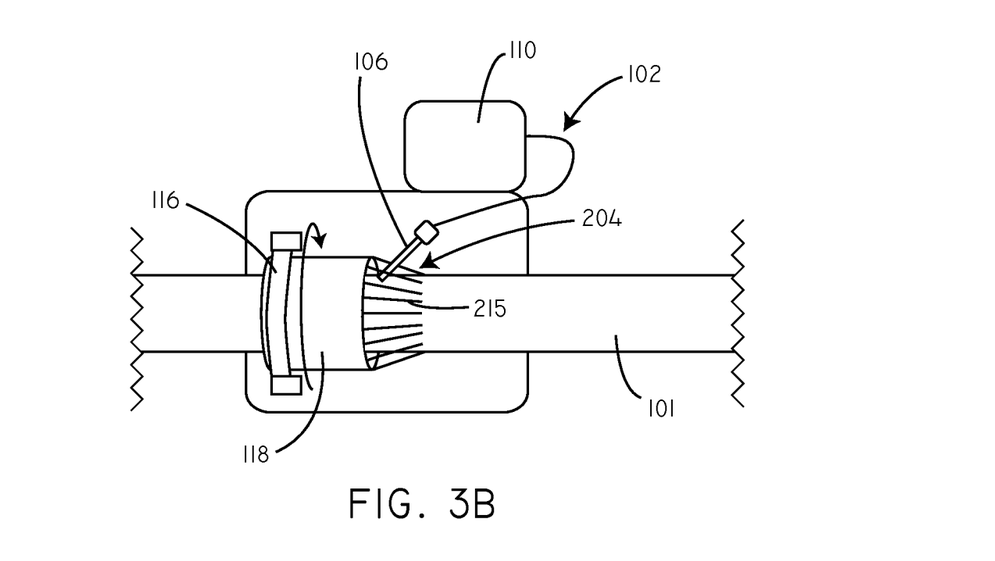
FIG. 3B is a schematic view of a coating apparatus in accordance with various embodiments herein.

FIG. 3B is a schematic view of a coating apparatus in accordance with various embodiments herein. The coating apparatus 102 includes a rotating contact member 204, a fluid applicator 106, a fluid pump 110, and a base member. The coating apparatus 102 can include mounting structure 116. The coating apparatus 102 can include drive shaft 118. The rotating contact member 204 can include bristles 215 or similar structure. The bristles 215 can contact the surface of the medical device 101 to be coated as the rotating contact member 204 rotates around and contacts the medical device 101 to be coated.

Figure 4:
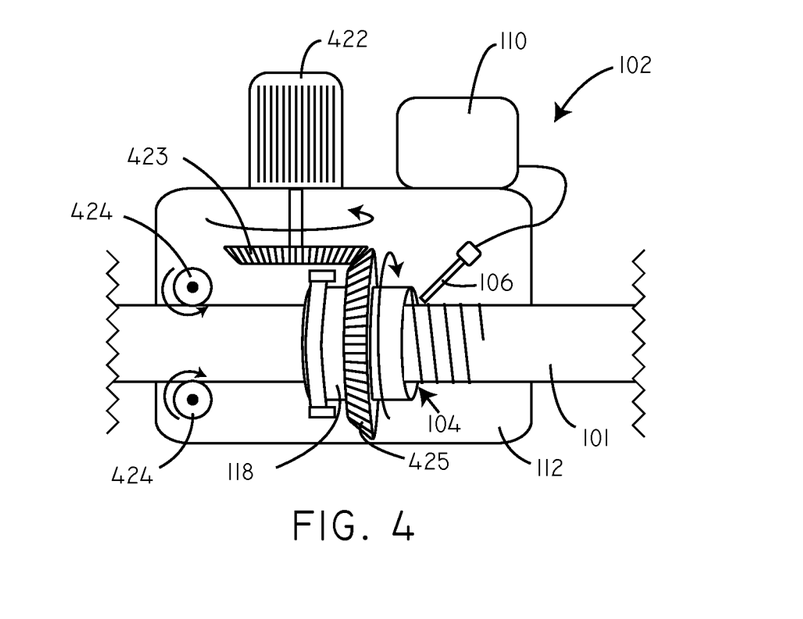
FIG. 4 is a schematic view of a coating apparatus in accordance with various embodiments herein.

FIG. 4 is a schematic view of a coating apparatus in accordance with various embodiments herein. The coating apparatus 102 includes a motor 422, a rotating contact member 104, a fluid applicator 106, a fluid pump 110, and a base member 112. The fluid applicator 106 includes an orifice. The coating apparatus 102 can include a mounting structure 116. The coating apparatus 102 can include drive wheels 424. The drive wheels 424 can contact the medical device 101 to be coated and can serve to push or pull the medical device 101 to be coated through the rotating contact member 104. The motor 422 can provide motive force to rotate the rotating contact member 104 and/or the drive wheels (or shafts) 424. By way of example, the motor 422 can be used to turn a drive gear 423 which can in turn drive an open center gear 425 causing the rotating contact member 104 to rotate. However, it will be appreciated that there are many different ways of conveying motive force from the motor 422 to the rotating contact member 104 including pulleys, belts, other types of gears, and the like. The motor 422 can be of many different types. In various embodiments the motor 422 can be an electric motor. In some embodiments, a motor can be omitted.

Figure 5:
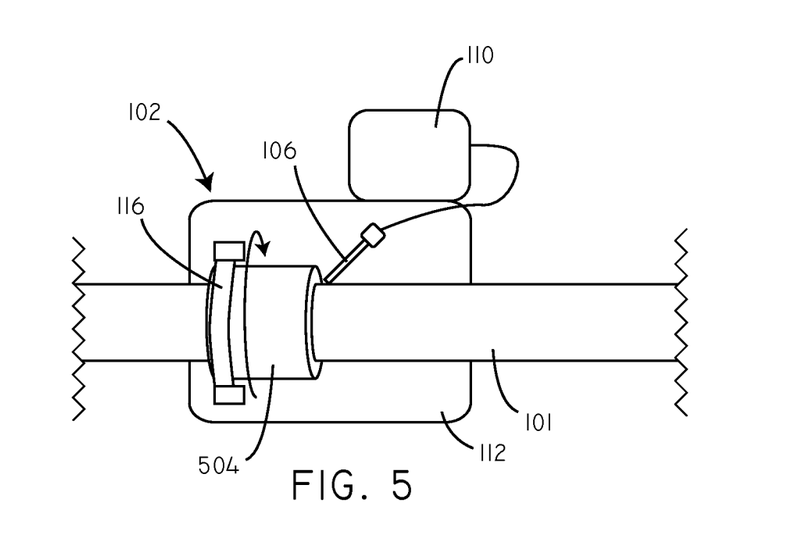
FIG. 5 is a schematic view of a coating apparatus in accordance with various embodiments herein.

FIG. 5 is a schematic view of a coating apparatus in accordance with various embodiments herein. The coating apparatus 102 includes a rotating contact member 504, a fluid applicator 106, a fluid pump 110, and a base member 112. The fluid applicator 106 includes an orifice. The coating apparatus 102 can include mounting structure 116. The rotating contact member 504 can have an inner diameter just slightly larger than the outside of the medical device 101 to be coated.

Figure 6:
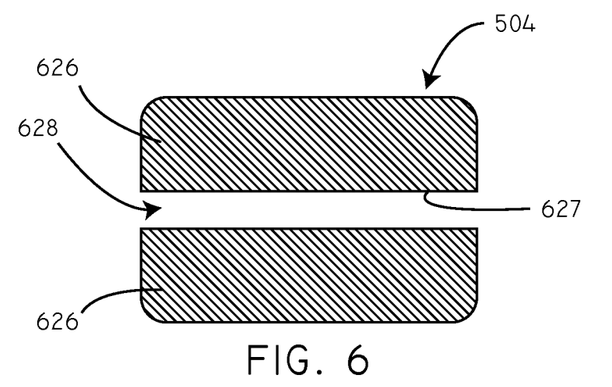
FIG. 6 is a schematic cross-sectional view of a rotating contact member in accordance with various embodiments herein.

FIG. 6 is a schematic cross-sectional view of a rotating contact member in accordance with various embodiments herein. The rotating contact member 504 can include a housing 626. The housing 626 can define a central lumen 628. The central lumen 628 can have a diameter sufficiently large so as to accommodate the outside diameter of the medical device 101 (not shown) to be coated. In some embodiments, the inner surface 627 of the central lumen 628 can be substantially smooth. In other embodiments, the inner surface of the central lumen 628 can include surface features. In some embodiments, the inner surface of the central lumen 628 can include thread-like projections similar to the inner diameter of a nut.

Figure 7:
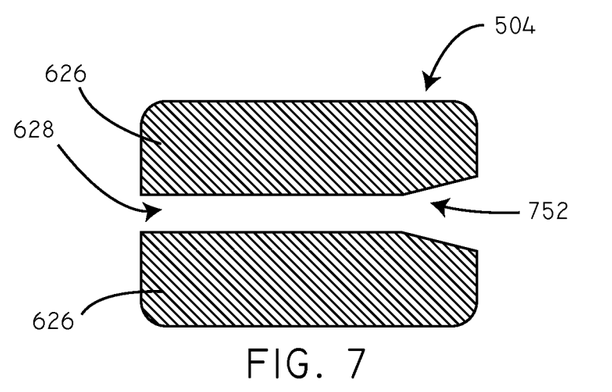
FIG. 7 is a schematic cross-sectional view of a rotating contact member in accordance with various embodiments herein.

In some embodiments, the central lumen can be substantially the same over the length of the rotating contact member. In other embodiments, different portions of the central lumen can be different. Referring now to FIG. 7, the rotating contact member 504 can include housing 626. The housing 626 can define central lumen 628. In this embodiment, the diameter of central lumen 628 is larger on one side of the rotating contact member 504 than on the other. In some embodiments, the central lumen 628 can have a tapered 752 or funnel-like shape on one side.

Figure 8:
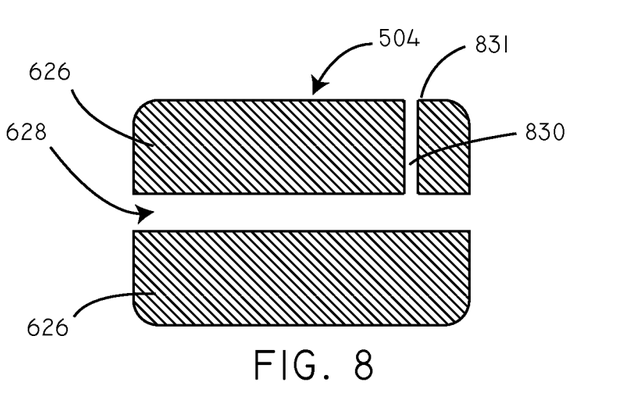
FIG. 8 is a schematic cross-sectional view of a rotating contact member in accordance with various embodiments herein.

In some embodiments, the coating material can be applied through the fluid applicator. However, in other embodiments, the coating material can be applied through other structures. Referring now to FIG. 8, the rotating contact member 504 can include a housing 626. The housing can define central lumen 628. The housing 626 can include fluid port 830. The fluid port 830 can provide fluid communication between the central lumen 628 and the exterior surface 831 of the rotating contact member 504. A coating composition can be supplied to exterior portion of the fluid port 830 and can then flow to the central lumen 628 where it can be applied to a device to be coated. In some embodiments multiple fluid ports 830 can be provided on the rotating contact member 504.

Figure 9:
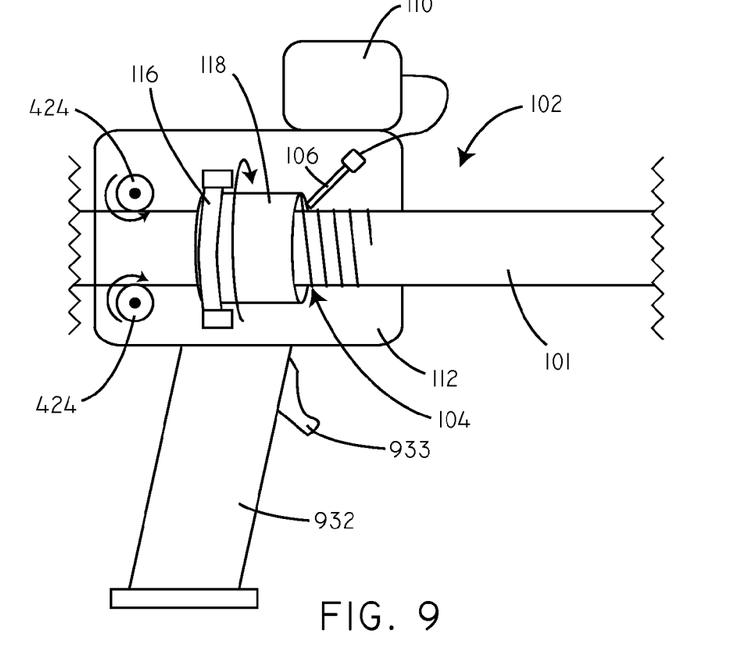
FIG. 9 is a schematic view of a coating apparatus in accordance with various embodiments herein.

Coating apparatus in accordance with embodiments herein can take on various configurations. In some embodiments, the coating apparatus can be hand held. Referring now to FIG. 9, the coating apparatus 102 includes a rotating contact member 104, a fluid applicator 106, a fluid pump 110, and a base member 112. The fluid applicator 106 includes an orifice. The coating apparatus 102 can include mounting structure 116. The coating apparatus 102 can include drive wheels 424, 424. The coating apparatus 102 can include drive shaft 118. The coating apparatus 102 can include a hand grip 932. The hand grip 932 can include a control element such as a trigger 933 to control operation of the apparatus.

Figure 10:
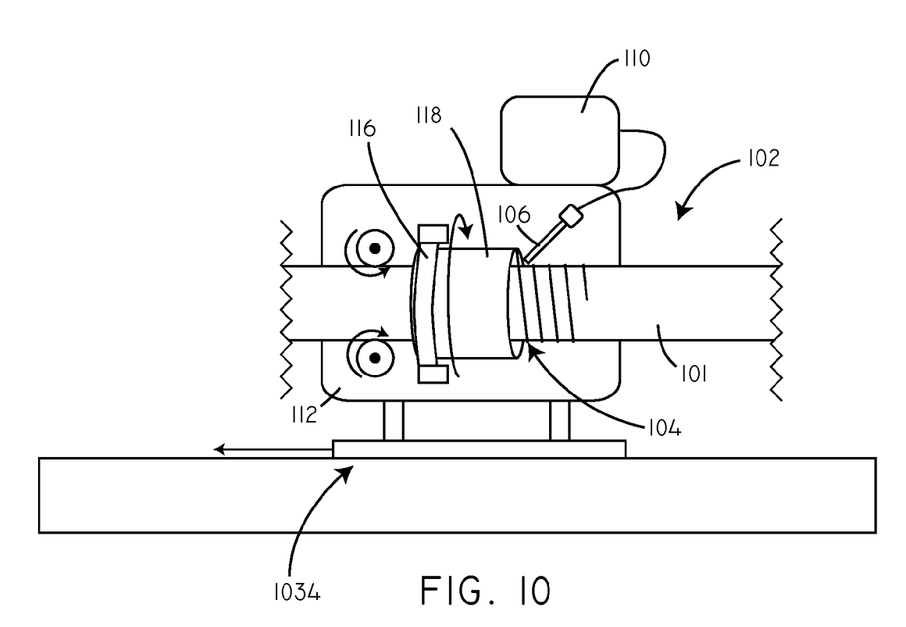
FIG. 10 is a schematic view of a coating apparatus in accordance with various embodiments herein.

In some embodiments, the apparatus can be mounted on a structure and move along the lengthwise axis of a device to be coated. Referring now to FIG. 10, the coating apparatus 102 includes a rotating contact member 104, a fluid applicator 106, a fluid pump 110, and a base member 112. The fluid applicator 106 can include an orifice. The coating apparatus 102 can include a mounting structure 116. The coating apparatus 102 can include drive wheels. The coating apparatus 102 can include drive shaft 118. The coating apparatus 102 can also include a linear actuator 1034. The linear actuator can provide motive force in order to move the coating apparatus linearly so as to provide movement along the lengthwise axis of the device 101 to be coated.

Figure 11:
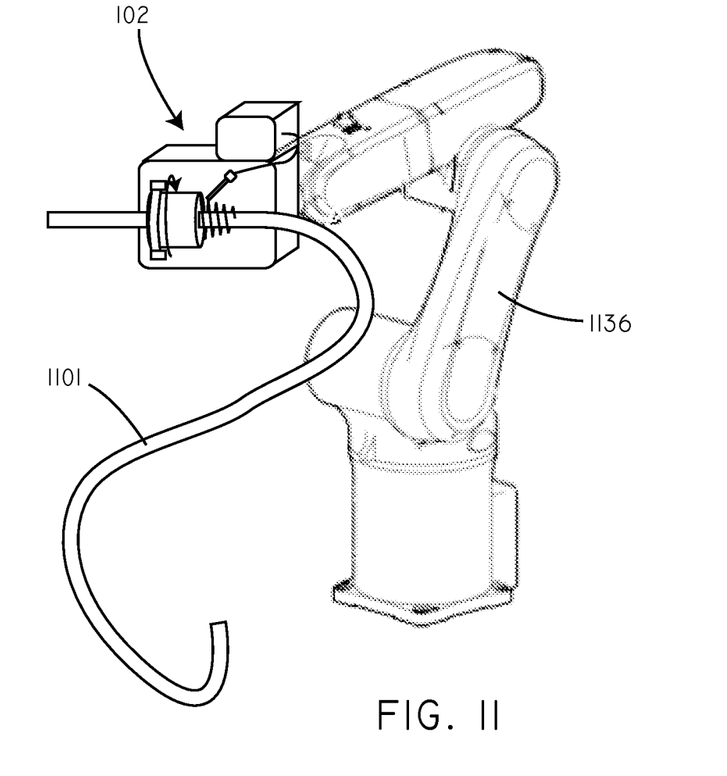
FIG. 11 is a schematic view of a coating apparatus in accordance with various embodiments herein.

FIG. 11 is a schematic view of a coating apparatus in accordance with various embodiments herein. In this embodiment the coating apparatus 102 includes a six-axis robot arm 1136. The robot arm 1136 can be used to move the coating apparatus 102 in such a way that it follows the contours of a medical device 1101 to be coated.

It will be appreciated that the rotating contact member can take on many different shapes and configurations. In some embodiments, the rotating contact member can have a spiral shape. For example, the rotating contact member can be a spiral-shaped element. The spiral-shaped element can include a flexible material. The spiral-shaped element can be formed of various materials including polymers, metals, and the like. In some embodiments, the spiral-shaped element is formed of a shape-memory metal. The spiral of the spiral-shaped element can include at least about two turns. In some embodiments, the spiral-shaped element is arranged so that rotation carries a coating composition along the surface of the device to be coated in the same direction along the lengthwise axis of the device as the rotating contact member moves. In other words, the spiral-shaped element can be used to push the coating material outward ahead of the oncoming rotating contact member versus pull the coating material inward toward the rotating contact member. However, in other embodiments, the orientation of the spiral-shaped element can be reversed so that it pulls the coating material in towards the rotating contact member.

The rotating contact member can include a housing in some embodiments. The housing can be made of many different materials including metals, polymers, composites, ceramics, and the like. In some embodiments, the housing can be formed of polytetrafluoroethylene. The housing can define a central lumen into which the device to be coated fits. The central lumen can have a larger diameter at one end than at the other. The central lumen can form a funnel shape in some embodiments. The funnel shape can be disposed at one end of the housing. The housing can also define a fluid port in some embodiments. The housing can be cylindrical in some embodiments The rotating contact member can rotate at a speed in the range of about 50 to 400 RPM. The rotating contact member can rotate at a speed of about 100 to 200 RPM. In some embodiments, the rotating contact member can rotate at a speed of greater than about 50 RPM. In some embodiments, the rotating contact member can rotate at a speed of greater than about 75 RPM. In some embodiments, the rotating contact member can rotate at a speed of greater than about 100 RPM. In some embodiments, the rotating contact member can rotate at a speed of greater than about 125 RPM. In some embodiments, the rotating contact member can rotate at a speed of less than about 400 RPM. In some embodiments, the rotating contact member can rotate at a speed of less than about 350 RPM. In some embodiments, the rotating contact member can rotate at a speed of less than about 275 RPM. In some embodiments, the rotating contact member can rotate at a speed of less than about 200 RPM.

The rotating contact member and/or the channel can be sized to accommodate a device to be coated having a diameter of between 0.5 mm and 20 mm. In some embodiments, the rotating contact member and/or the channel can accommodate a device to be coated having a diameter greater than about 0.5 mm. In some embodiments, the rotating contact member and/or the channel can accommodate a device to be coated having a diameter greater than about 1 mm. In some embodiments, the rotating contact member and/or the channel can accommodate a device to be coated having a diameter greater than about 3 mm. In some embodiments, the rotating contact member and/or the channel can accommodate a device to be coated having a diameter less than about 15 mm. In some embodiments, the rotating contact member and/or the channel can accommodate a device to be coated having a diameter less than about 11 mm. In some embodiments, the rotating contact member and/or the channel can accommodate a device to be coated having a diameter less than about 8 mm. In some embodiments, the rotating contact member and/or the channel can accommodate a device to be coated having a diameter between about 0 mm and about 15 mm. In some embodiments, the rotating contact member and/or the channel can accommodate a device to be coated having a diameter between about 1 mm and about 11 mm. In some embodiments, the rotating contact member and/or the channel can accommodate a device to be coated having a diameter between about 3 mm and about 8 mm.

The coating apparatus can include drive wheels in various embodiments (such as that shown in FIG. 9. The drive wheel can contact the device to be coated can generate force to push or pull the device to be coated through the apparatus. In some embodiments, the drive wheel pulls the device to be coated through the rotating contact member. In some embodiments, the drive wheel can be substantially smooth. In some embodiments, the drive wheel can include a surface texture. The drive wheel can be formed of various materials. In some embodiments, the drive wheel can be formed of silicone (PMDS).

The apparatus can move along the lengthwise axis of the device to be coated at various speeds through the action of the drive wheels or another source of motive force. In some embodiments, the apparatus can coat that device to be coated at a speed of between 0.1 and 1.5 cm per second.

In some embodiments, the apparatus can coat a device to be coated at a speed of greater than 0.1 cm/s. In some embodiments, the apparatus can coat a device to be coated at a speed of greater than about 0.5 cm/s. In some embodiments, the apparatus can coat a device to be coated at a speed of greater than about 1.0 cm/s. In some embodiments, the apparatus can coat a device to be coated at a speed of less than about 2 cm/s. In some embodiments, the apparatus can coat a device to be coated at a speed of less than about 1.5 cm/s. In some embodiments, the apparatus can coat a device to be coated at a speed of less than about 1 cm/s. In some embodiments, the apparatus can coat a device to be coated at a speed of between about 0 cm/s and about 2 cm/s. In some embodiments, the apparatus can coat that device to be coated at a speed of between about 0.1 cm/s and about 1.5 cm/s. In some embodiments, the apparatus can coat that device to be coated at a speed of between about 0.5 cm/s and about 1 cm/s.

In some embodiments, the rotating contact member can assume an open configuration and a closed configuration. In some embodiments, the device to be coated can be inserted or removed from the rotating contact member when it is in the open configuration.

In some embodiments, the coating apparatus can include a drive shaft. The drive shaft conveys motive force between the motor and the rotating contact member. The drive shaft can be hollow. In some embodiments, the device to be coated can be disposed within the rotating contact member and/or the drive shaft such that the rotating contact member and/or the drive shaft rotates around the device to be coated.

In an embodiment, the invention includes a method of coating a medical device. The method of coating a medical device can include rotating a contact member around the outer diameter of a non-rotating medical device. The method can further include applying a coating solution to the outer diameter of the non-rotating medical device at a position adjacent to the contact member. The method can further include moving at least one of the contact member and the non-rotating medical device with respect to one another so that the contact member moves with respect to the lengthwise axis of the non-rotating medical device.

In some embodiments, rotation of the spiral shaped contact member causes the coating composition to move along the surface of the non-rotating medical device in the same direction along the lengthwise axis of the non-rotating medical device as the rotating contact member moves. In some embodiments, applying a coating solution comprises applying the coating solution onto the rotating contact member. In other embodiments, applying a coating solution comprise applying the coating solution directly onto the device to be coated. In some embodiments, an operation of inserting the non-rotating medical device into the contact member can be performed before the step of rotating the contact member.

Medical Devices

The coating apparatus of embodiments herein allows the precise application of coating materials onto medical devices with an extraordinary degree of control regarding where the coating stops and starts along the length of the medical device, uniformity of the coating applied and the amount of coating applied.

Many different types of medical device can be coated with apparatus described herein. By way of example, medical devices coated in accordance with embodiments described herein can include devices having a degree of curvature and/or stiffness such that they cannot practically be spun- or dip-coated. In a particular embodiment, the device can be one including a curved shaft. In some embodiments, the device can be one that lacks a central lumen.

In some embodiments, the present apparatus and coating methods can be used to coat catheters for transaortic valve implants (TAVI; see SAPEIN trancatheter heart valve; available from Edwards Lifesciences Corporation, Irvine, Calif.). TAVI devices and procedures can be used in cases where patients have severe aortic stenosis but where those patients are not candidates for surgery. TAVI catheters typically are not straight and have three dimensional bends or curves. The catheters are curved in order to assist the physician in the accurate placement of the valve at the site of the stenosis. There is a need to apply hydrophilic coatings to TAVI catheters to improve lubricity upon delivery of the TAVI to the site.

In the past, coating these non-linear, highly curved catheters using traditional methods such as dip or spray coating has resulted in coatings that are inconsistently applied or that require inordinate amount of waste coating material compared to the coating material applied to the surface of the medical device. Apparatus and methods of the present disclosure can be used to accurately apply a coating to the surface of TAVI devices with bends and curves, since apparatus and methods disclosed herein are largely not dependent upon the spatial configuration of the medical device to achieve accurate surface coatings.

In yet other embodiments, the medical device to be coated can be a balloon catheter. The balloon catheter can be coated in the apparatus described herein in the collapsed state. Alternatively, the balloon catheter can be coated in the apparatus described herein in the partially or fully expanded state. In one embodiment, the balloon catheter can be coated with a bioactive material such as a chemical ablative (e.g. vincristine, paclitaxel) and used for renal artery denervation therapy for hypertension.

Coating Solutions

It will be appreciated that coating solutions applied onto balloons can include various components including, but not limited to, one or more active agents, carrier agents, solvents (aqueous and/or non-aqueous), polymers (including degradable or non-degradable polymers), monomers, macromere, excipients, photoreactive compounds, linking agents, and the like. The relative amounts of the components of the coating solution will depend on various factors.

The coating solutions can be formulated so as to provide various functional properties to the medical device to which they are applied. By way of example, the coating solutions can be formulated so as to provide lubricious properties; anti-infective properties, therapeutic properties, durability and the like.

In other embodiments, the coating solution has relatively low viscosity. By way of example, in some embodiments, the coating solution can have viscosity of less than about, 100 50, 40, 30, 20, or 10 centipoise. In some embodiments, the coating solution can have a viscosity of between about 1 and 100 centipoise.

In some embodiments, the coating solution can have a solids content that is relatively low. By way of example, in some embodiments, coating solutions used in conjunction with embodiments herein can have a solids content of less than about 10 mg/ml. In some embodiments, coating solutions used in conjunction with embodiments herein can have a solids content of less than about 5 mg/ml. In some embodiments, coating solutions used in conjunction with embodiments herein can have a solids content of less than about 2 mg/ml.

It should be noted that, as used in this specification and the appended claims, the singular forms 'a,' 'an,' and 'the' include plural referents unless the content clearly dictates otherwise. Thus, for example, reference to a composition containing 'a compound' includes a mixture of two or more compounds. It should also be noted that the term 'or' is generally employed in its sense including 'and/or' unless the content clearly dictates otherwise.

It should also be noted that, as used in this specification and the appended claims, the phrase 'configured' describes a system, apparatus, or other structure that is constructed or configured to perform a particular task or adopt a particular configuration to. The phrase 'configured' can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The invention claimed is:

1. A coating apparatus comprising:
   a motor;
   a rotating contact member in mechanical communication with the motor, the rotating contact member configured to rotate around a device to be coated that does not rotate, the rotating contact member also configured to move relative to the device to be coated along a lengthwise axis of the device to be coated;
   a fluid applicator comprising an orifice adjacent to the rotating contact member;
   a fluid pump in fluid communication with the fluid applicator; and
   a base member supporting the rotating contact member and the fluid applicator.

2. The coating apparatus of claim 1, the rotating contact member comprising a spiral shape.

3. The coating apparatus of claim 2, the rotating contact member comprising a spiral shaped wire.

4. The coating apparatus of claim 3, the spiral shaped wire comprising a shape memory metal.

5. The coating apparatus of claim 3, the spiral oriented so that rotation carries a coating composition along the surface of the device to be coated in the same direction along the lengthwise axis of the device to be coated as the rotating contact member moves.

6. The coating apparatus of claim 1, the rotating contact member comprising a channel into which a device to be coated fits.

7. The coating apparatus of claim 1, the rotating contact member comprising a plurality of bristles.

8. The coating apparatus of claim 1, the rotating contact member comprising a brush.

9. The coating apparatus of claim 6, the rotating contact member comprising a housing, the channel comprising a central lumen defined by the housing.

10. The coating apparatus of claim 9, wherein the diameter of the central lumen is larger at one end than the other.

11. The coating apparatus of claim 9, the lumen comprising a funnel shape at one end of the housing.

12. The coating apparatus of claim 9, wherein the housing is cylindrical.

13. The coating apparatus of claim 1, wherein the rotating member rotates at a speed of 50 to 400 rotations per minute.

14. The coating apparatus of claim 1, wherein the rotating member rotates at a speed of 100 to 200 rotations per minute.

15. The coating apparatus of claim 6, wherein the channel accommodates a device to be coated having a radius of between 0.5 mm and 20 mm.

16. The coating apparatus of claim 1, further comprising a drive wheel contacting the device to be coated, wherein the drive wheel pulls or pushes the device to be coated through the rotating contact member.

17. The coating apparatus of claim 16, wherein the drive wheel pulls the device to be coated through the rotating contact member at a speed of between 0.1 and 1.5 cm/s.

18. The coating apparatus of claim 1, wherein the rotating contact member moves between an open configuration and a closed configuration, wherein the device to be coated is inserted or removed from the rotating contact member when it is in the open configuration.

19. The coating apparatus of claim 1, further comprising a drive shaft that conveys motive force between the motor and the rotating contact member, wherein the drive shaft is hollow and a portion of the device to be coated is disposed within the drive shaft.

20. The coating apparatus of claim 1, the base including a hand grip.

21. The coating apparatus of claim 1, the base mounted on a six-axis robot arm.

* * * * *